United States Patent [19]

Lützen

[11] 4,316,956
[45] Feb. 23, 1982

[54] FERMENTATION PROCESS
[75] Inventor: Niels W. Lützen, Ballerup, Denmark
[73] Assignee: Novo Industri A/S, Denmark
[21] Appl. No.: 119,034
[22] Filed: Feb. 6, 1980
[51] Int. Cl.$^3$ ............................................. C12P 19/20
[52] U.S. Cl. ..................................... 435/96; 435/99; 435/161
[58] Field of Search .................... 435/96, 42, 99, 161, 435/162, 813; 426/11, 13, 14, 29, 494

[56] References Cited

U.S. PATENT DOCUMENTS

| | | | |
|---|---|---|---|
| 2,342,330 | 2/1944 | Christensen | 435/161 |
| 3,922,197 | 11/1975 | Leach et al. | 435/96 |
| 4,009,074 | 2/1977 | Walon | 435/94 |
| 4,009,075 | 2/1977 | Hoge | 435/162 |
| 4,092,434 | 5/1978 | Yoshizumi | 426/14 X |
| 4,235,965 | 11/1980 | Walon | 435/99 |

*Primary Examiner*—R. B. Penland
*Attorney, Agent, or Firm*—Fidelman, Wolffe & Waldron

[57] ABSTRACT

This invention relates to a novel fermentation process and in particular, to fermentative production of ethanol producing in the presence of non-gelled, or granular, starch particles, alpha-amylase and a glucoamylase; characteristic of the present process is recycle of enzymes for renewed use in fermentation, usually through termination of the fermentation prior to complete disappearance of the granular starch particles, and recovery for use anew of the unconsumed starch, along with enzymes thereon. Fermentation according to practice of this invention proceeds at a near to linear rate in the main.

8 Claims, 9 Drawing Figures

FERMENTATION PROCESS

BACKGROUND OF THE INVENTION

The conventional fermentation for the production of an ethanol containing solution must operate within the conditions required for cultivating the ethanol producing microorganism, e.g., *Saccharomyces cerevisiae* including, for example, maintenance of pH between about 3 and 7, maintenance of a temperature range between about 25° C. and 38° C., commencement of the fermentation with a wort containing not more than about 20% glucose by weight and avoidance of any efforts to generate more than about 10% by weight of alcohol in the fermentation broth.

In the great many instances wherein starch or a starchy substance such as corn grits is the source of the glucose consumed in the fermentation, the process includes a starch liquefaction and hydrolysis sequence to convert the (solid) starch into a glucose solution that becomes, in part at least, the growth medium for the yeast.

While starch conversion into glucose and maltose for fermentation purposes has been carried out on a large scale for eons in commercial practice, the procedures employed in prior art practices rarely convert starch completely into fermentable sugars. Even relatively minor deficiencies in conversion of starch into the fermentables, maltose and glucose, have adverse affect on the fermentation, the least of which is lower yield than would otherwise result, and/or a greater processing expense. For example, the traditional process for making beer wherein grains are hydrolyzed by malt results in a wort with a significant nonfermentable polysaccharide content, and, in turn, a beer with a significant polysaccharide content.

This situation has, of course, received considerable attention from workers in the pertinent arts.

On the whole, it is fair to state that starch liquefaction and hydrolysis procedures capable of producing a pure glucose syrup are available, as for example, liquefaction of starch according to the procedures described in U.S. Pat. No. 3,912,590 followed by saccharification according to the procedures described in U.S. Pat. No. 4,017,363. However, all of the starch liquefaction and hydrolysis procedures known to the inventor hereof can be criticized for requiring moderate to large quantities of thermal energy.

It should be noted moreover that fermentation of starch derived glucose syrups, whether of high purity or otherwise, face the microorganism with the presence of a very large excess of the glucose nutrient at the onset of the fermentation, little nutrient at the termination of fermentation, and otherwise comply with a need to avoid commencement of the fermentation with a syrup containing more than about 20% dissolved carbohydrate.

Insofar as the inventor herein is aware, the existence of disadvantages in fermenting a completely saccharified starch have received relatively little attention from the art. Instead the art has concerned itself with improving liquefaction, e.g., U.S. Pat. No. 3,912,590, saccharification to pure glucose, e.g., U.S. Pat. No. 4,017,363, resolving processing difficulties, e.g., U.S. Pat. Nos. 3,922,196 to 3,922,201 and 4,009,074; and with avoiding high thermal energy requirements for starch liquefaction and saccharification, e.g., U.S. Pat. No. 4,092,434. Some of the above referenced U.S. Pat. Nos., particularly 4,009,074 and 4,092,434, teach that ungelatinized starch, i.e., granular starch can be liquefied enzymatically at relatively low temperatures.

However, the inventor herein is not aware of any efforts by the art to integrate low temperature enzymatic liquefaction of starch with conduct of the fermentation so as to achieve improvements in the fermentation process, e.g., improved fermentation efficiency, and/or reduced fermentation time, and/or fermentation with a fermentation broth containing more than about 25% solids content. The last reduces water and energy costs.

The rationale of the present invention derives from a discovery that the fermentation may be carried out on a slurry of solid and completely ungelled starch, i.e., granular starch, dosed with alpha-amylase and glucoamylase. During the course of the fermentation the starch is enzymatically liquefied and saccharified into fermentable sugars and the sugars are fermented. Control over the fermentation rate is possible through variations in the starch concentration in the slurry, by preconditioning of the starch, and through variations in the concentration and proportions of alpha amylase and glucoamylase in the slurry.

OBJECTS OF THE INVENTION

The principle object of this invention is to provide an improved fermentation process adapted for fermentation conversion of granular starch into ethanol.

One object of this invention is to provide a fermentation process with improved thermal efficiency.

Another object of this invention is to provide a rapid fermentation procedure.

An additional object of this invention is to provide a fermentation process that ferments a broth containing therein more than 25% by weight of substances convertible to ethanol.

Further objects and the advantages of this invention will become apparent from the description which follows.

BRIEF STATEMENT OF THE INVENTION

Briefly stated, the present invention involves use of a fermentation medium which contains suspended granular starch particles, alpha-amylase, and a glucoamylase. The enzymes are relied upon to liquefy the solid starch particles and to saccharify the dissolved starch to the fermentables glucose and maltose during the course of the fermentation.

The proportions of granular starch in the medium and of each enzyme are set to provide a controlled release of fermentables to the yeast, allowing thereby control over the fermentation reactions. Characteristic of practice of the present invention is recovery of enzymes from the fermentation medium for use anew. Any undissolved starch particles remaining in the fermentation broth at the time the fermentation is halted contain thereon considerable amounts of alpha-amylase. Removal of residual starch particles from the fermentation broth for a later refermentation is a preferred way to recover enzymes.

According to one preferred embodiment of the invention, the enzymatic liquefaction, saccharification and fermentation circumstances are set to generate alcohol at near to a linear rate over the principal course of the fermentation.

Optionally, the present process contemplates a pretreatment step in which a starch slurry is treated with an alpha-amylase and, optionally, a glucoamylase at temperatures below the initial gelatinization point of granular starch. (Which temperature is conventionally given as being not less than about 62° C. for cornstarch.) The pretreatment generates a small proportion of fermentables in the slurry so that the microorganism has nutrient immediately available for initiating fermentation.

GENERAL DISCUSSION OF THE INVENTION

For further understanding of this invention reference is now being made to the attached drawings wherein.

Fermentation according to practice of this invention depends upon conducting all of the sequential reactions involved in converting granular starch into ethanol inside the same pot under the temperature and pH circumstances of 25°–38° C., pH 3–7 adapted to cultivation of the alcohol producing microorganisms such as saccharomyces. The reactions may be described as follows:

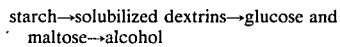

starch→solubilized dextrins→glucose and maltose→alcohol

Figure 1:
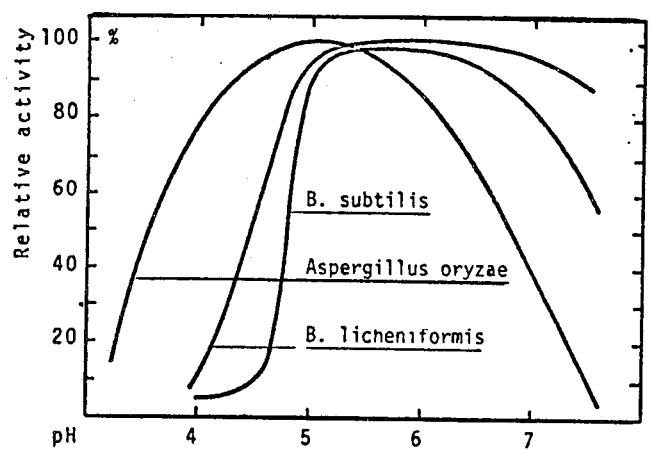
FIG. 1 is a graph showing pH v. activity for representative alpha-amylases at 37° C.

As may be seen in FIG. 1, the activity of typical commercially available alpha-amylase enzymes on dissolved starch at pH 3.5 to 6, and 37° C. is substantial. The test methods were the Novo FA-Method, which is a modification of the classic Sandstedt, Kneen and Blish (SKB) analysis. However, results comparable to the curves shown in FIG. 1 will be obtained with any test method. Once the starch has been liquefied, the alpha-amylase contributes significantly to hydrolysis of the dextrins into fermentable sugars at fermentation pH and temperature conditions.

Figure 2:
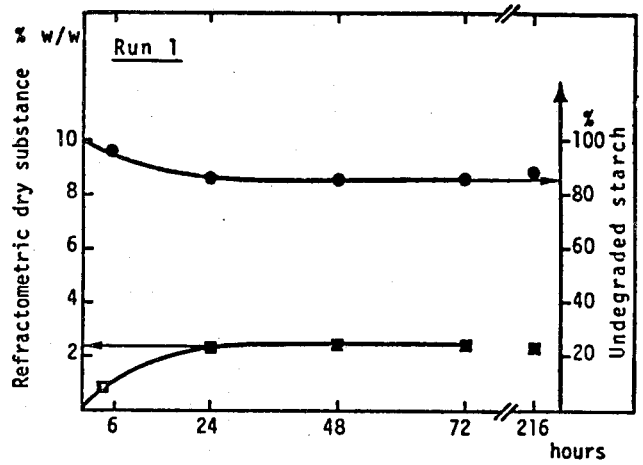
FIG. 2 is a graph showing disappearance of solid starch from starch slurried at 34° C. and in the presence of alpha-amylase over a period of time (Example 9, run 1).
Figure 4:
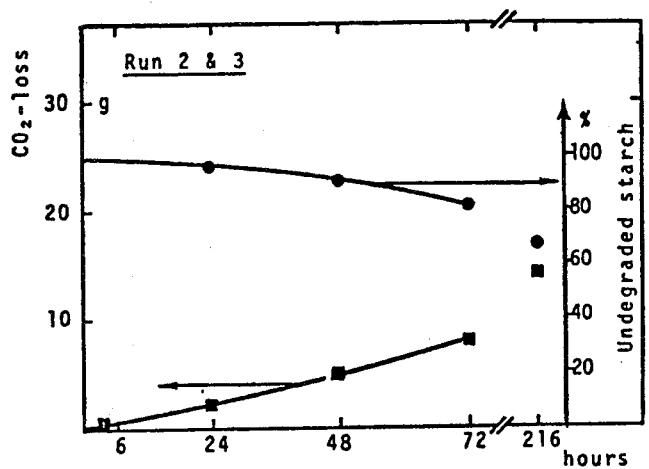
FIG. 4 is a graph showing the disappearance of starch under the conditions of the FIG. 2 graph when the slurry is fermented (Example 9, runs 2 and 3).

It has not been widely appreciated heretofore that alpha-amylase liquefies granular starch at a significant reaction rate. FIG. 2 shows both the cumulative disappearance of solid ungelled starch i.e., granular starch, over a period of time at 34° C. and, the corresponding increase in dissolved carboyhydrate. It is noteworthy tht (under the conditions tested, see Example 9 hereinafter) while the alpha-amylase dissolved only about 20% of the granular starch after 216 hours, when fermentation is carried out with a like slurry close to 40% of the granular starch had gone into solution after 216 hours. The fermentation results are illustrated in the graph of FIG. 4.

Figure 3:
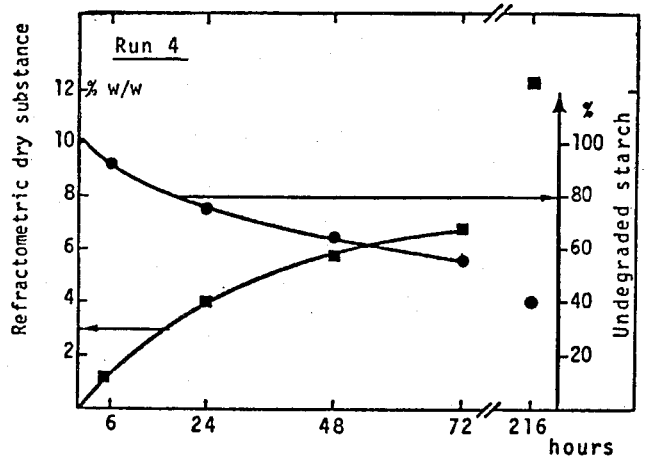
FIG. 3 is a graph showing disappearance of solid starch under the conditions of the FIG. 2 graph when glucoamylase is also present (Example 9, run 4).
Figure 5:
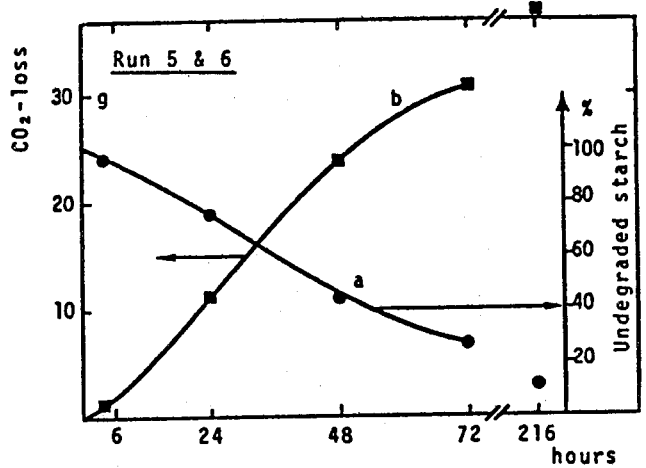
FIG. 5 is a graph showing the disappearance of solid starch under the conditions of the FIG. 3 graph when the slurry is fermented (Example 9, runs 5 and 6).

Inclusion of glucoamylase along with the alpha-amylase in the starch slurry produces more striking results. As can be seen from the test results illustrated in FIG. 3, (also Example 9 hereinafter) a combination of alpha-amylase and glucoamylase can dissolve about 60% of the granular starch in the slurry over 216 hours. Concurrently fermenting removed about 90% of the granular starch from the slurry, as is illustrated in FIG. 5.

The progression of from 20% to more than 90% disappearance of granular starch from a slurry under the cumulative influence of alpha-amylase, glucoamylase and fermentation demonstrates the feasibility of a single pot conversion of granular starch into ethanol. Moreover since enzyme concentration and proportions and starch concentration may be varied at will, a high degree of engineering flexibility exists for practice of this invention.

Conduct of the liquefaction hydrolysis and fermentation reactions concurrently inside the fermentor has numerous theoretical and practical points of superiority over conduct of the same reactions in three separate stages, the system heretofore employed to the greatest extent. On the whole, as may be noted from the results illustrated by FIGS. 1–4, concurrent conduct of the reactions accelerates the liquefaction and hydrolysis conversion reactions, thereby generating several points superiority for the process of this invention over prior art practices.

Thus, liquefaction of starch to a (hot) dextrin solution has long faced both product loss and processing difficulties due to occurrence of starch retrogradation reactions in the hot dextrin. The concurrent liquefaction of the starch and saccharification of the dextrins which take place according to practice of this invention avoid conditions conducive to the starch reversion reactions.

Concurrent conduct of all the reactions at fermentation temperatures will, of course, save significant quantities of thermal energy, since the starch slurry need not be subjected to the elevated temperatures conventionally employed to liquefy starch. For instance, eliminating a conventional starch cooking process which cooks at 140° C. is estimated to save about 700 K cal per kg of ethanol product, which saving compares favorably to the about 7000 K cal per Kg combustion energy of ethanol.

A separate advantage is that any (non-dissolved) granular starch remaining at the expiration of the fermentation has not been degraded or even gelled (by a thermal treatment). Such starch may be recovered readily, then resuspended and cycled through the process as if it were fresh granular starch. Recycle of granular starch is contemplated for practice of this invention.

Conversion of dextrins into glucose when carried out by a microbial glucoamylase (AMG) on high solids content syrups is accompanied by an enzyme catalyzed reverse reaction wherein glucose polymerizes into polysaccharides such as isomaltose, a sugar which is non-metabolizable by the yeast. The reaction rate of the reversion reactions is some function of glucose concentration in the syrup. Therefore, a concurrent generation of glucose and fermentative removal of glucose from the syrup should prevent even a small loss in fermentables due to glucose reversion reactions.

Fermentative conversion of the usual saccharified dextrin solution to alcohol often faces the yeast with more than enough carbohydrate nutrient i.e., of glucose and maltose, in the early stages of fermentation and a deficiency of carbohydrate nutrient in the late stages of fermentation. Practice of this invention avoids the excess of available carbohydrate nutrient during the early stages and, makes fermentable sugars available to the yeast during the late stages.

The ultimate fermentation broth can be expected to contain some of each of the individual materials in the above reaction sequence. It is noteworthy that the solid starch particles may be separated out easily (by centrifugation for example). The ethanol may be separated out easily (by distillation for example). The yeast can be counted upon to minimize the glucose content in the fermentation broth. Only the dextrins can neither be separated out readily, nor be converted by the yeast.

The dextrin content in the ultimate fermentation broth represents, at least potentially, a loss in the system. Accordingly, a preferred practice of this invention involves enzyme concentrations and proportions for an essentially complete rapid saccharification of the dextrins into fermentable sugars, so that dextrin content in the fermentation medium is maintained at a low level throughout the fermentation. Since the metabolic transformations carried on by the yeast insure that the glucose disappears quickly, the fermentation medium contains little glucose and dextrins at all times and over the course of the fermentation, considerable granular starch in ever decreasing amounts, and ethanol in ever increasing amounts.

ENZYME CONSIDERATIONS

Allusion has already been made as to how practice of this invention involves fermenting at the temperature and pH circumstances that are optimum for the ethanol producing microorganism, i.e., pH 3–7, 25°–38° C. Although the fermentation circumstances are not also optimum temperatures and pH for state-of-the-art commercially available alpha-amylases and glucoamylases, such enzymes are effective for practice of this invention in economically realistic enzyme concentrations. Actually, the pH conditions for fermentation do correspond closely to the optimum pH for commercially available saccharification enzymes, i.e., the glucoamylases. In the present process complete saccharification to glucose is favored by the gradual solubilization of granular starch which takes place. Presumably then, the enzyme always faces dextrin in low concentration. In addition, fermentation removal of the glucose throughout the fermentation maintains a low glucose content in the fermentation medium. The glucoamylase also faces glucose in low concentration. In consequence, the glucoamylase is used so effectively that economically feasible dosage levels of glucoamylase (AMG) can be employed for practice of this invention, namely a glucoamylase dosage of 0.05–10.0 AGU/g of starch preferably 0.2–2.0 AGU/g starch.

One AG unit (AGU) is the amount of enzyme which splits one micromol of maltose per minute at 25° C. and pH 4.3. A commercially available liquid form of glucoamylase (AMG NOVO 150) has an activity of 150 AGU per ml. (See Ford et al, Biochem Vol. 54 (1973) 120.)

The dosages provided above for glucoamylase only approximate the effective concentration of the enzymatic saccharification activity in the fermentation broth. Some unknown proportion of the saccharification activity is contributed by the alpha-amylase. Commercially available alpha-amylases will produce significant amounts of sugars, such as glucose and maltose, as is evidence on FIGS. 2 and 4.

Indeed, addition of the alpha-amylase from *Aspergillus oryzae* (e.g., Fungamyl ®) to wort has been suggested to the brewing industry. This particular enzyme saccharifies dextrins to maltotriose and maltose. Thus, although the purpose of the alpha-amylase is to liquefy the starch, its saccharification propensity also make the alpha-amylase some part of the saccharifying enzyme content.

On the other and, less than all of the glucoamylase dose added to the granular starch slurry may be active in catalyzing saccharification reactions in the solution. The glucoamylase proportions between starch solids and the liquid. A set of measurements carried during fermentation of a 20% by weight starch suspension indicated that about 70% of the glucoamylase is present in the liquid phase 6 hours after initiating fermentation, and about 85% is present after 72 hours. The results are illustrated in FIG. 6.

Figure 6:
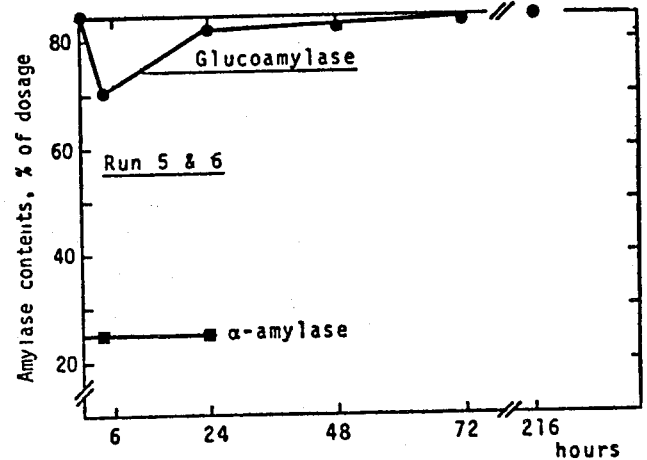
FIG. 6 is a graph showing the amylase and glucoamylase activity in the fermentation broth over the course of the fermentation illustrated by FIG. 5.

The results illustrated in FIG. 6 indicate, also that little, if any, loss of dissolved enzyme has occurred after 216 hours of fermentation. Accordingly, removal of the ethanol product from the fermentation broth by a recovery technique that does not subject the fermentation broth to temperatures that deactivate the glucoamylase enzyme, e.g., distillation under vacuum, allows recovery of the dissolved glucoamylase for use anew in fermentation of particulate starch.

A further point of interest to practice of this invention is that commercially available glucoamylases contain some alpha-amylase activity, and indeed, it is possible, but not practical, to ferment particulate starch in the presence solely of glucoamylase.

For practice of this invention, addition of alpha-amylase to the slurry of particulate starch is contemplated. With certainty all that can be said is than an effective amount of alpha-amylase is added. Aside from the uncertain amount of alpha-amylase activity contributed by the glucoamylase, the effective activity of the alpha-amylase may be quite different from the unit activity values given by the supplier. The activity of alpha-amylase is pH dependent, and as is illustrated by FIG. 1 for three diverse commercially available alpha-amylases, may be different at the pH range selected for the fermentation, than at the test conditions employed by the suppliers for their reported unit activity values. Trial and error tests can readily establish the most effective dosages for alpha-amylases not herein exemplified.

In any event the alpha-amylase dosage range for fungal alpha-amylases contemplated for practice of this invention is 0.02 FAU/g (Fungal Amylase Units) to 2.0 FAU/g of starch, preferably 0.05–0.6 FAU/g. One FAU is the amount of enzyme which breaks down 5260 mg of starch per hour under a standardized set of conditions. One FAU corresponds to approximately 25 SKB units, see Cerial Chemistry, Vol. 16 (1939) page 712-723. For Bacillus alpha-amylases the range is 0.01 KNU/g to 0.6 KNU/g, preferably 0.05 to 0.15 KNU/g, the NU (or Novo Unit) being the amount of enzyme which breaks down 5.26 mg of starch per hour under a standardized set of conditions. One KNU is 1000 NU.

The uncertainty as to the real activity of both the glucoamylase and the alpha-amylase in the fermenting slurry will require some cut and try experimentation to achieve acceptably optimum operating conditions for any particular commercial installation constructed for practice of this invention. Some guidelines can be provided for optimization test efforts.

Increasing the alpha-amylase dosage with a constant glucoamylase content, increases the fermentation rate. Increasing the glucoamylase dosage with a constant alpha-amylase content increases the fermentation rate. Holding enzyme dosage constant, and increasing the starch content in the slurry increases the fermentation rate.

When all is said and done, the optimum alpha-amylase dosage may well exceed dosages heretofore recommended for liquefying starch; the optimum glucoamylase may well exceed dosages recommended for saccharifying syrups. However, enzyme dosage levels should not be confused with enzyme usage. Substantial proportions of the enzymes dosed into the starch slurry may be enzyme recovered from the fermentation broth for use anew to ferment granular starch.

A further consideration arising from employment of the enzymes at fermentation temperatures is that although the enzymes exhibit low relative activity, for example, activity of the alpha-amylase from *B. licheniformis* at fermentation temperatures is not more than about 25% of maximum activity, the low relative activity is counterbalanced by the extended duration of the 48–120 hours of fermentation, and by the extended half-life of enzymes that have not been subjected to elevated temperatures. As near as can be ascertained more than 90% of the enzymes activity remains after 72 hours of fermentation.

The alpha-amylase of *B. licheniformis* (e.g., Termamyl ®), is sufficiently stable to withstand brief exposures to still pot temperatures. Thus, recycle of stillage can be used as a way to recycle alpha-amylase. In the main, however, recovery of enzyme in recycled stillage will require care to avoid subjecting the fermentation broth to ethanol stripping temperatures that deactivate the enzymes. The alcohol might, for example, be vacuum stripped from the fermentation broth and such stillage recycled to recover the enzymes.

A particularly advantageous way to recover enzymes for reuse, particularly the alpha-amylase is to conduct the fermentation so as to leave some granular starch in the fermentation broth when fermentation is halted. As is illustrated in FIG. 6, the alpha-amylase proportions itself between the granular starch solids and the solution with only about 25% of the alpha-amylase dosage to be found in the liquid (using the Phadebas ® Amylase test, a variant of the method mentioned by Ceska et al Clin. Chim. Acta, Vol. 26 (1969) p. 437). Accordingly, recovering residual granular starch for renewed fermentation recycles a large proportion of the alpha-amylase, and a minor proportion of the glucoamylase.

It should, of course, be appreciated that the dosage ranges for both alpha-amylase and of glucoamylase described above are intended to be the total of recycled and freshly added enzymes.

PROCESS CONSIDERATIONS

As has already been pointed out, fermentation of a granular starch slurry has completely different characteristics than fermentation of a syrup. Generally about 20% solids in solution is considered the maximum sugar content in a fermentation medium with higher concentrations creating difficulties at the onset and at the end of fermentation. No like limits exist on fermentation of a starch slurry. Concentration of starch in the slurry may vary from 10–45% with no discernable consequence at the onset of fermentation. Increasing starch concentration (at constant enzyme dosages) speeds up the fermentation rate, or conversely, allows for lowering the enzyme dosages required to achieve a given fermentation rate. In any event fermenting until the broth has 7–10% alcohol, as is prevalent in the fermentation arts, is still possible. The excess (residual) granular starch may be recovered, along with substantial amounts of enzymes and subjected to renewed fermentation. Thus, control over starch concentration is a major process parameter for practice of this invention.

One preferred mode of this invention is fermentation of a granular starch slurry having 25–40% starch by weight.

Fermenting a 25–40% starch slurry with common baker's yeast will invariably result in residual starch when fermentation has proceeded to the intended alcohol content levels e.g., 7–10% dependent on the microorganism used and, therefore, recycle of the enzymes on the starch particles occurs when the residual starch is again fermented. However, even when a 10–25% starch slurry is fermented, preferred practice of this invention is to halt fermentation before complete disappearance of the granular starch, for fermentation anew. Recycling of starch is a facile way to recover enzymes for reuse.

According to one preferred mode of this invention, the (granular) starch and yeast are removed together, e.g., by centrifugation, and along with fresh granular starch and makeup enzymes become the fermentation charge.

Figure 9:
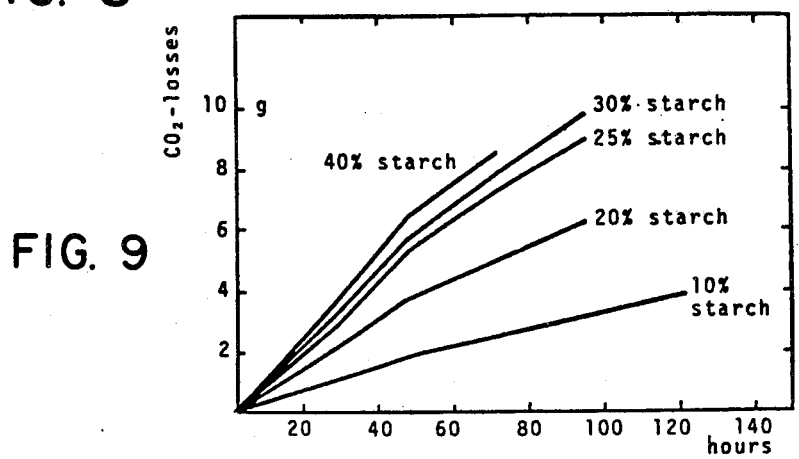
FIG. 9 is a graph showing the effect on fermentation results of different starch concentrations (Example 11).

Another difference between fermentation of granular starch according to practice of this invention and fermentation of a sugar syrup is that the granular starch slurry will normally be fermented at near to a linear rate during the main course of the fermentation. At the onset of fermentation a lag period may exist, while near the end of the fermentation the alcohol content may have built up to levels that interfere with the fermentation. In between, i.e., during the main course of the fermentation, the fermentative release of carbon dioxide and buildup of ethanol content proceed at near to a linear rate as is illustrated by FIGS. 4, 5 and 9. The linearity may be difficult to avoid in the starch slurry fermentation system of this invention, since fermenting slurries of different initial starch concentrations at any given enzyme dosage alters the fermentation rate, but does not alter the near to linearity at which $CO_2$ is generated. Changing enzyme proportions alters the fermentation rate without, it seems, altering the near to linear generation of $CO_2$ during the main fermentation.

It is believed that the near to linear rate of fermentation herein achieved is attributable to a near to linear rate at which the granular starch liquefies. The dextrins content in the fermentation broth is low (e.g., about 0.25%) during the main fermentation, as is the glucose content. The low measured dextrin and glucose levels leave liquefaction of granular starch as the limiting reaction, and, if linear, the reason for a linear fermentation rate. Conduct of fermentation at a near to linear rate as is a preferred practice of this invention is then keyed to having granular starch always present in the fermentation broth during the main fermentation.

The main fermentation can be considered to end at a level of alcohol content of about 7%, where common baker's yeast is unable to consume the maltose and glucose nutrient as rapidly as the enzymes generate available nutrient through liquefaction and saccharification. Consequently, the fermentation rate (as measurable by $CO_2$ production) decreases and linearity is lost. The fermentation may be allowed to continue thereafter (at a non-linear rate) until the desired alcohol content in the fermentation broth is reached, and doing so is contemplated in practice of this invention.

Deviations from linearity in the fermentation rate as will typically occur at the end of the fermentation can cause buildup of carbohydrates in solution, both of fermentables and polysaccharides. Some engineering expedients (individually and in combination) contemplated for use in practice of this invention to avoid loss of the dissolved nutrients are:

(1) removing the starch (after the main fermentation) then continuing to ferment the starch free broth.

(2) vacuum stripping the fermentation broth to reduce alcohol content so that the microorganisms can function more effectively;

(3) recycling nutrient containing still bottoms for renewed fermentation.

To a large extent engineering trade-offs will be required in arriving at optimum process details, and the trade-offs may vary for each particular installation. For instance to achieve the most rapid fermentation reasonable, high starch content, high enzymes dosage are indicated, but then the consequential rapid fermentation tails off into generation of a level of nutrients in the fermentation broth that dictates recovery of the nutrients, or, alternatively that fermentation be halted at a relatively low alcohol content. If relatively low fermentation rates are acceptable, then (with high starch content slurries) enzyme dosage is relatively low and nutrient losses can be held to levels heretofore accepted by the fermentation arts. If maximum yield of alcohol is a principal objective, then low starch content slurries, moderate alpha-amylase dosage, high glucoamylase dosage might be employed.

In any event, preferred practice of this invention is to halt fermentation while granular starch yet remains in the fermentation broth. The granular starch residue is removed and fermented anew. Much of the alpha-amylase and a minor proportion of the glucoamylase are recovered thereby. Ordinarily, recovery of the starch will also remove from the fermentation broth much, or even all of the alcohol producing microorganisms. Starch and microorganism may be separated, if desired, but seeding a fermentation charge with recycled granular starch and microorganisms removed with the starch is desirable for practice of this invention.

Allusion has already been made as to how practice of this invention saves considerable thermal energy. However, just as the starch is never subjected to the thermal conditions used for liquefactions, the starch is not thermally sterilized. In all likelihood the granular starch will add contaminating microorganisms to the fermentation medium. Under the circumstances then, seeding the fermentation medium with the great number of the ethanol producing microorganism that might accompany recycled granular starch can be advantageous. Through their great numbers, the recycled microorganisms overwhelm any contaminating microorganisms, thereby dominating the fermentation, as is, of course, desired.

Allusion has been made to the brief lag phase that has been observed at the onset of fermentation in almost all instances. During the lag phase multiplication of the microorganisms takes place and/or carbohydrate nutrients are generated from the granular starch. Pretreatment of the starch slurry with either or both enzymes for up to 20 hours at from 30° C. to 60° C. will serve to hasten the commencement of fermentative generation of ethanol in the fermentor. The enzymatic pretreatment serves to generate carbohydrate nutrient in the slurry before the microorganisms are introduced.

EXEMPLARY PRACTICES OF THE INVENTION

Figure 7:
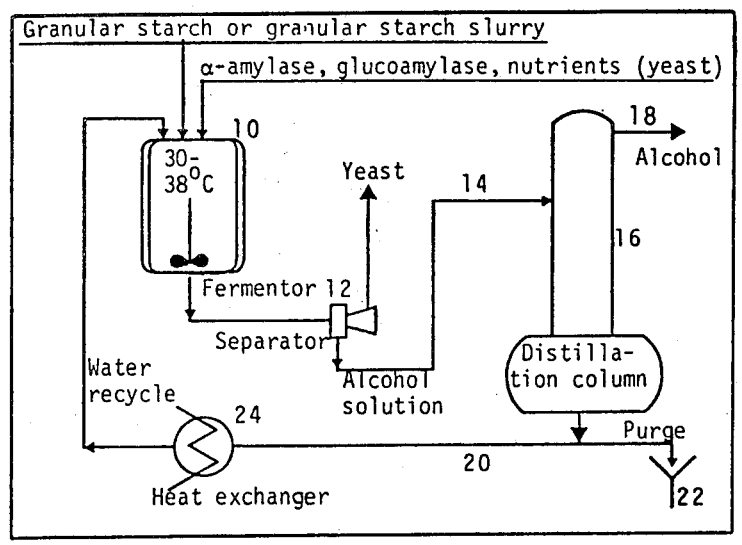
FIG. 7 is a flow sheet showing one mode of how fermentation of granular starch is integrated with an alcohol distillation.

One preferred mode of the present invention is illustrated in FIG. 7 wherein it can be seen that alpha-amylase, glucoamylase, water with essential nutrients therein, granular starch and an ethanol producing microorganism, e.g., brewer's yeast, are all added to batch fermentor 10. An essentially concurrent addition of all the ingredients is contemplated. Thereafter fermentation is carried out at usual temperature and pH conditions for ethanol production, e.g., at pH 5, 38° C. over a suitable period of time, e.g., 160 hours. Then the fermentation mixture is subjected to centrifugation in centrifuge 12, to separate yeast and any unconverted starch particles from the fermentation broth. The fermentation broth then passes by way of line 14 directly into still 16, wherein the alcohol content is stripped for removal overhead in line 18. The stillage is taken off as bottoms through line 20. Some of the stillage is recycled by way of heat exchanger 24 to become part of the feed water for the fermentation, and the balance of the stillage is discarded through line 22, as a purge stream.

The system illustrated by FIG. 7 is particularly adapted to the instances where a single pass complete conversion of the granular starch is desired, as would take place when a 10–20% starch slurry is fermented. The mode of FIG. 7 is particularly adapted also to use therein of thermally stable alpha-amylases, since such enzymes (e.g., Termamyl ®) can withstand brief exposure to still pot temperatures. The enzymes notably the thermally stable alpha-amylase are returned to fermentor 10 in the water recycle.

The mode of FIG. 7 can be operated as a continuous fermentation, in which instance fermentor 10 might, for example, be modified so as to provide an elongated path for the fermenting slurry to travel (in plug flow) from inlet to outlet.

Figure 8:
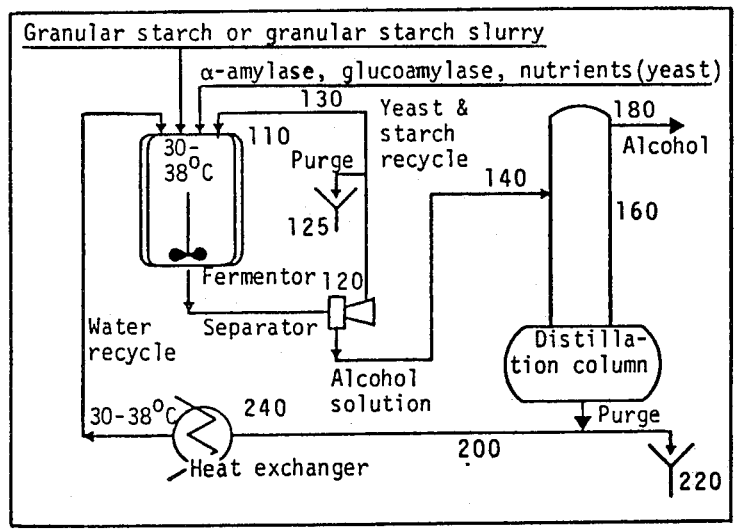
FIG. 8 is a flow sheet showing another mode of integrating the fermentation of granular starch with an alcohol distillation.

FIG. 8 illustrates a mode wherein fermentation is halted when unconverted granular starch yet remains in the fermentation broth. Fresh granular starch, enzymes and optionally yeast are charged into fermentor 110, along with recycled yeast and granular starch. The fermented broth passes to centrifugal separator 120 wherein yeast and unconverted granular starch are separated out for recycle by way of line 130 back to fermentor 110. Some of the yeast and starch is removed to a purge line 125. The centrifuged broth passes by way of line 140 into still 160 for separation into the alcohol overhead, removed through line 180, and still bottoms, removed by way of line 200. Some of the stillage is purged through line 220, while the balance is cooled in heat exchanger 240 before return to fermentor 110. The mode of FIG. 8 can, of course, be constructed for continuous operation.

Since as much as 75% of the alpha-amylase and about 15% of the glucoamylase values are recoverable in the starch recycle, the mode of FIG. 8 can be employed with a heat labile alpha-amylase. Complete thermal inactivation in still 160 of the alpha-amylase left in the centrifuged broth can be tolerated. Indeed, recycle of stillage may be omitted altogether in practice of the mode of FIG. 8.

By and large, the mode of FIG. 8 is intended for fermenting high starch concentration slurries; 20-45% being the general range contemplated; 35-40% being the preferred range. Conveniently, the starch slurry from a wet corn milling operation can be fed directly into a fermentation system adapted to practice of this invention, e.g., the mode of FIG. 8. The solids content of a wet mill starch slurry is close to 40% starch by weight.

The quantities of yeast initially charged into the fermentation vat may be in accord with prior art practices for ethanol fermentation, and can vary widely since the yeast cells will multiply during the course of the fermentation. Recycle of yeast cells is not necessary. Removal of the yeast from the residual starch particles prior to recycling of the residual starch is contemplated. However, it is noted once again that practice of the present invention do not include inherently a thermal treatment of the starch i.e., thermal conditions that would heat sterilize the starch. It might well be advisable to charge relatively large proportions of yeast cells into the fermentation in order to help overcome the likelihood of (inadvertent) contamination. Antibiotics may be added to the fermentation medium to suppress growth of contaminating microorganisms, and cold sterilization techniques could, of course, be employed on the entering materials.

As has already been pointed out, practice of this invention controls the fermentation rate by releasing metabolizable sugars to the yeast at a controlled rate. This is different from what has been done heretofore. The objectives of prior art suggestions to treat solid starch with enzymes prior to fermentation and/or to include enzymes in the fermentation medium are to conserve energy and/or to improve fermentation efficiency, but are not suggestions to alter the character of the fermentation so as to achieve a near to linear fermentation rate. Certainly practice of the present invention conserves energy as compared to high temperature starch liquefaction. If anything, more thermal energy is conserved. The present process operates with high fermentation efficiency, in part because product losses due to starch retrogradation incomplete saccharification and incomplete fermentation of fermentables may be reduced. The ability to tailor the fermentation rate through control of starch concentration and enzymes content and proportions includes the capability of creating in the end a fermentation broth product with minimal carbohydrate content.

Thus, vis a vis prior art suggestions which superficially resemble some of the practices of this invention, the more comprehensive objectives of this invention are reflected into a great many detail features believed to be unique to practice of this invention, including notably enzyme recycle and starch recycle.

SPECIFIC EXAMPLES

For further understanding of this invention the following specific examples of practice thereof are posed.

EXAMPLE 1

A slurry containing 50 g granular corn starch (91.3% dry substance) in 150 g water, is adjusted to a $Ca++$ content of 7 mg/l (in final volume) and pH to pH 5. 65 μl Termamyl® 60 L (alpha-amylase) and 135 μl of Spiritamylase® 150 L (glucoamylase) are added. The final weight is adjusted to 250 g by addition of water, and the supension stirred on a water bath for 18 hours at 60° C.

After 18 hours, 150 ml of the slurry (approximately 162 gm) are transferred to a fermentation flask cooled to 30° C. and to the flask are added:

2 ml yeast extract solution (20 g DIFCO yeast extract in 100 ml of distilled water 2 ml antibiotics (1.25 g Streptomycin, +1.25 g penicillin in 150 ml distilled water)

5 ml yeast suspension (6 g bakers yeast/100 ml distilled water)

Spiritamylase-150 L (glucoamylase) as in Table 1.

The flask is equipped with a magnetic stirring rod, and fitted with a fermentation trap containing 98% sulphuric acid. After an initial weighing, fermentation is conducted at 30° C. for 6 days and the weight loss of $CO_2$ is measured by weighing the flask from time to time over the 6 days. The results are tabulated below:

TABLE 1

| Run | AMG-150 | $CO_2$ Weight Loss | | | | RTS* |
|---|---|---|---|---|---|---|
| | | 18h | 91h | 115h | 138h | 138h |
| 1 | 65 μl | 4.94g | 14.22 | 14.36 | 14.52 | 3.35% |
| 2 | 130 μl | 5.46 | 14.36 | 14.57 | 14.64 | 2.10% |

*Residual Total Sugar given in % of original starch feed, the amount of starch being converted to equivalent, weight of glucose The analytical method used is the Minnesota method for the determination of total sugars (Whistler & Wolfrom: Methods in Carbohydrate Chemistry I, 1962 p. 388).

The measured RTS values cover both dextrines and granular starch as no filtration of the media is performed. (Note that in the following Table 8 B, the dextrin content in the fermentation is measured after filtering the fermentation broth, i.e., eliminating the contribution of the granular starch).

EXAMPLE 2

To a slurry of 30 g granular corn starch (91.3% dry substance) in 140 g water adjusted to 7 mg $Ca++/l$ and pH5 is added 30 μl (0.1% on dry substance) Termamyl ® 60L. (alphaamylase) then stirred at 60° C. for 18 hours.

After the 18 hours pre-treatment, the flask is cooled to between ambient and 30° C., then yeast extract, antibiotics and yeast are added as in example 1. After addition also of 50 μl (0.165% on dry substance) of Spiritamylase ® 150L (glucoamylase), the flask is fitted with a fermentation trap containing 98% sulphuric acid. After weighing, the flask is placed on a magnetic stirring device and fermented at 30° C. for 160 hours. The weight losses of $CO_2$ are measured by weighing from time to time. After 111 hours of fermentation approximately 50 grams of slurry is withdrawn and analyzed for total sugars content and for alcohol content (by cryostatics). (In further conduct of this run corrections are made for the withdrawn material.) At the end of the fermentation, at 160 hours, the analysis is repeated. The results are tabulated below.

TABLE 2

| Run No. | Cumulative $CO_2$ losses in grams: | | | | |
|---|---|---|---|---|---|
| | 24h | 87h | 111h | 136h | 160h |
| 1 | 5.78g | 12.31 | 12.83 | 12.68 | 12.69 |
| 2 | 5.42g | 11.85 | 12.57 | 12.47 | 12.48 |

Alcohol Content

TABLE 2-continued

| Run No. | RTS 110h | RTS 160h | % w/w 110h | % w/w 160h |
|---|---|---|---|---|
| 1 | 5.2% | 4.3% | 10.50% | 10.77% |
| 2 | 7.2% | 6.4% | 10.22% | 10.55% |

The fermentation was repeated with a split in glucoamylase addition, 25 μl being added in the pretreatment and 25 μl being added with the yeast. Except for a somewhat larger $CO_2$ production during the first 24 hours, and a greater RTS content in the fermentation broth, the alcohol yield and cumulative $CO_2$ production were similar to the results reported above in Table 2.

EXAMPLE 3

The fermentations described in Example 2 were repeated substituting however, 30 μl of BAN 120L (an alpha-amylase from *B. subtilis*) for the 30 μl of Termamyl ® (an alpha-amylase from *B. licheniformis*).

The results are tabulated below.

TABLE 3A

| Cumulative $CO_2$ losses | | | | RTS | | Alcohol Content % w/w | |
|---|---|---|---|---|---|---|---|
| 24h | 87h | 111h | 160h | 110h | 160h | 110h | 160h |
| 5.24 | 12.13 | 12.80 | 13.21 | 5.7% | 3.54% | 10.28% | 10.54% |

The results obtained when addition of the glucoamylase is split between the pretreatment and the fermentation are tabulated below.

TABLE 3B

| Cumulative $CO_2$ losses | | | | RTS | | Alcohol Content % w/w | |
|---|---|---|---|---|---|---|---|
| 24h | 87h | 111h | 160h | 110h | 160h | 110h | 160h |
| 5.75 | 11.28 | 12.14 | 12.55 | 9.1% | 7.03% | 10.17% | 10.45% |

EXAMPLE 4

A comparative test was carried out comparing conduct of a fermentation with liquefied starch and with solid starch according to the present process.

A. Liquefied Starch 30 g of corn starch (91% dry solids content) slurried in 140 g of water, pH adjusted to pH 5 and 7 mg $Ca^{++}$ added was dosed with 30 μl of Termamyl ® 60L, then the slurry was heated in a stirred laboratory autoclave at 2° C./minute to 100° C. and held at 100° C. for 30 minutes. The sample was weighed and the water loss (through evaporation) was replaced. The solution was cooled to 30° C. then dosed and fermented as in Example 1.

B. Solid Starch

A like 30 g starch of slurry with 30 μl Termamyl ® was stirred for 21 hours at 60° C. on a water bath, then cooled to 30° C., dosed and fermented as in Example 1. The results are tabulated below.

TABLE 4

| Run No. | Procedure | $CO_2$ Losses After 19h | 45h | 114h | 138h |
|---|---|---|---|---|---|
| 1 | B | 4.24 | 8.37 | 12.69 | 13.03 |
| 2 | B | 4.05 | 8.27 | 12.60 | 12.90 |
| 3 | B | 4.10 | 8.19 | 12.69 | 13.09 |
| 4 | A | 3.83 | 8.72 | 11.66 | 11.65 |
| 5 | A | 3.28 | 6.92 | 11.30 | 11.31 |
| 6 | A | 3.08 | 8.22 | 12.96 | 13.08 |

A high residual sugar content in the fermentation broth in runs 4 and 5 (procedure A) is believed to indicate that a significant level of starch retrogradation occurred.

EXAMPLE 5

The pretreatment and fermentation of Example 2 was repeated, except that the 60° C. pretreatment was carried out at pH 5 and at pH 6 to ascertain whether the optimum pH activity pattern of the enzyme was material in starch treatment at below the temperature of starch gelation. The results tabulated below indicate that treatment at the pH optimum for the enzyme is nominally superior.

TABLE 5

| Run No. | Initial pH | Cumulative $CO_2$ losses 17h | 41h | 70h | 166h | RTS in % |
|---|---|---|---|---|---|---|
| 1 | 5 | 3.90 | 7.97 | 10.38 | 12.3 | 5.3% |
| 2 | 5 | 3.84 | 7.78 | 10.33 | 12.3 | 4.5% |
| 3 | 6 | 3.88 | 7.50 | 10.00 | 12.11 | 5.7% |
| 4 | 6 | 3.91 | 7.79 | 10.34 | 12.15 | 6.3% |

EXAMPLE 6

A. The pretreatment and fermentation of Example 2 was repeated with the 60° C. pretreatment time varied between 3 hours and 20 hours.

The results as tabulated below indicate surprisingly little differences between a 3 hour pretreatment and a 20 hour pretreatment.

TABLE 6A

| Run No. | γ-amylase Treatment at 60° C., hrs. | Weight losses as $CO_2$ 17h | 41h | 70h | 166h | RTS content after 166 hrs. % of starch |
|---|---|---|---|---|---|---|
| 1 | 20 | 3.90 | 7.97 | 10.38 | 12.30 | 5.3% |
| 2 | 20 | 3.78 | 7.73 | 10.18 | 12.24 | 5.4% |
| 3 | 6 | 3.71 | 7.33 | 10.30 | 12.07 | 4.5% |
| 4 | 6 | 3.76 | 7.17 | 9.65 | 11.85 | 7.9% |
| 5 | 3 | 3.76 | 7.28 | 9.99 | 11.62 | 9.3% |
| 6 | 3 | 3.69 | 7.32 | 9.97 | 10.48 | 3.4% |

B. The pretreatment was omitted entirely, with the yeast, granular starch and enzymes all mixed directly at 30° C. into the fermentation medium. The results are tabulated below.

TABLE 6B

| Run No. | Weight losses as $CO_2$ 17h | 41h | 70h | 166h | RTS content after 166 hrs. % of starch |
|---|---|---|---|---|---|
| 1 | 1.25 | 3.75 | 6.56 | 11.52 | 7.0% |
| 2 | 1.32 | 3.82 | 6.64 | 11.79 | 5.5% |

EXAMPLE 7

This example illustrates the use of different alpha-amylases at varying dosage levels. The pretreatment quantities and conditions, except as tabulated below, were those described in Example 2.

TABLE 7A

| | γ-amylase dosage in % of dry matter | | | | |
|---|---|---|---|---|---|
| Run No. | Termamyl® 60L | BAN 120L | Fungamyl® 800L | pH | Temp. |
| 1 | 0.1%, 30μl | | | 5 | 60° C. |
| 2 | | 0.1%, 30μl | | 5 | 60° C. |
| 3 | | 0.1% | | 6 | 60° C. |
| 4 | | 0.05% | | 6 | 60° C. |
| 5 | | | 0.02% | 5 | 55° C. |
| 6 | | | 0.01% | 5 | 55° C. |

As in Example 2, the α-amylase treated samples were submitted to fermentation at 30° C. after addition of glucoamylase, yeast, yeast extract anc antibiotics. The results are tabulated below:

TABLE 7B

| Run No. | Weight losses as $CO_2$ | | | | RTS content after 166 hrs. % of starch |
|---|---|---|---|---|---|
| | 17h | 41h | 70h | 166h | |
| 1 | 3.82 | 7.94 | 10.56 | 12.41 | 7.1% |
| 2 | 3.57 | 7.36 | 10.19 | 12.37 | 6.6% |
| 3 | 3.81 | 7.94 | 10.84 | 11.43 | |
| 4 | 3.64 | 7.34 | 10.11 | 12.25 | 7.3% |
| 5 | — | — | 8.15 | 11.98 | 4.5% |
| 6 | 2.38 | 5.57 | 8.64 | 12.46 | 6.2% |

EXAMPLE 8

This example illustrates the use of high starch content in the fermentation, with and without pretreatment.

The pretreatment quantities and conditions, except as tabulated below, were those described in Example 2.

The amount of glucoamylase added in connection with the fermentation is also shown below.

TABLE 8A

| Run No. | Pretreatment at 55° C. | % Starch | Fungamyl® 800L. | Glucoamylase AMG-150L in fermentation |
|---|---|---|---|---|
| 1 | None | 20% | 10 μl | 50 μl |
| 2 | None | 20% | 20 μl | 50 μl |
| 3 | None | 20% | 20 μl | 100 μl |
| 4 | None | 40% | 20 μl | 50 μl |
| 5 | None | 40% | 40 μl | 100 μl |
| 6 | None | 20% | None | 50 μl |
| 7 | None | 20% | None | 100 μl |
| 8 | None | 40% | None | 100 μl |
| 9 | None | 40% | None | 200 μl |
| 10 | $4\frac{1}{2}^h$ | 20% | None | 100 μl* |
| 11 | $4\frac{1}{2}^h$ | 20% | 20 μl | 50 μl* |

*Glucoamylase added in connection with pretreatment.

As in Example 2, the samples are submitted to fermentation at 30° C. after addition of glucoamylase yeast, yeast extract and antibiotics.

Weight loss, glucose in solution, total sugars in solution (dextrins and glucose) are analyzed during the fermentation.

TABLE 8B

WEIGHT LOSSES AND SUGAR CONTENTS DURING FERMENTATION

| | WEIGHT LOSSES AS $CO_2$ | | | | DEXTRINS AND GLUCOSE IN AQUEOUS PHASE | | | |
|---|---|---|---|---|---|---|---|---|
| | | | | | SUGAR ANALYSES 69h | | SUGAR ANALYSES 138h | |
| RUN NO. | 16h | 43h | 69h | 138h | GLUCOSE % | TOTAL SUGAR | GLUCOSE % | TOTAL SUGAR |
| 1 | 1.24g | 3.30 | 4.76 | 7.60 | 0.006% | 0.11% | 0.010% | 0.14% |
| 2 | 1.73g | 3.81 | 5.30 | 8.36 | 0.004% | 0.10% | 0.009% | 0.15% |
| 3 | 2.38 | 5.17 | 7.18 | 10.40 | 0.008% | 0.15% | 0.004% | 0.14% |
| 4 | 2.34 | 4.23 | 5.84 | 8.25 | 0.009% | 0.22% | 1.76% | 2.07% |
| 5 | 3.41 | 6.61 | 8.77 | 10.69 | 0.24% | 0.49% | 3.87% | 4.07% |
| 6 | 0.49 | 1.93 | 3.44 | 7.48 | 0.005% | 0.10% | 0.007% | 0.14% |
| 7 | 0.88 | 2.97 | 5.35 | 9.81 | 0.005% | 0.10% | <0.001% | 0.15% |
| 8 | 1.29 | 4.31 | 6.77 | 10.91 | 0.009% | 0.17% | 1.88% | 2.07% |
| 9 | 2.54 | 7.69 | 9.88 | 10.35 | 2.48% | 2.72% | >8.17% | 8.34% |
| 10 | 2.42 | 4.90 | 6.87 | 10.08 | 0.017% | 0.15% | 0.002% | 0.14% |
| 11 | 1.46 | 3.46 | 5.04 | 8.05 | 0.007% | 0.13% | <0.001% | 0.13% |

The possibility of fermenting higher concentrations of starch than about 20% is demonstrated.

The low levels of glucose and dextrins (Total Sugar) during the fermentation is also demonstrated.

It can be seen that for a constant enzyme dosage per ml of suspension, increasing the starch content in the slurry increases the fermentation rate.

Increasing the alpha-amylase content for a constant glucoamylase content increases the fermentation rate. The same observation is made for increasing the glucoamylase content for a constant alpah-amylase concentration.

It can be observed that the glucoamylase AMG-150L is able to act as the only enzyme in the fermentation. This is due to the fact that AMG-150L contains alpha-amylase activities besides the main glucoamylase activity. The influence of the pretreatment is a steeper initial fermentation. The fermentation curves ($CO_2$ versus time) show parallel slopes after the initial steep rise of the dosages of alpha-amylase and glucoamylase are equal.

EXAMPLE 9

This example illustrates the combined effect of the amylases and the yeast compared to the effect of amylase alone without fermentation.

No pretreatment of the starch with amylases. Both the hydrolysis and fermentation are run at 34° C. The starch content is 20% in this experiment, but 90 g are used (portions tripled compared to Example 2). In order to get quick fermentations, the yeast content is five times the content in Example 2; initial pH is 4.5

TABLE 9

EXPERIMENTAL CONDITIONS

| Run No. | γ-amylase Fungamyl® 500 L | Glucoamylase AMG | Kind of Treatment | Analyzed for |
|---|---|---|---|---|
| 1 | 120 μl | None | Saccharification | Refractometric dry Subst. |
| 2 | 120 μl | None | Sacch. + Ferment | $CO_2$ losses |
| 3 | 120 μl | None | Sacch. + Ferment | γ-amylase activity, alcohol cont. |
| 4 | 120 μl | 300 μl | Saccharification | as (1) |

TABLE 9-continued

| | EXPERIMENTAL CONDITIONS | | | |
|---|---|---|---|---|
| Run No. | γ-amylase Fungamyl® 500 L | Gluco-amylase AMG | Kind of Treatment | Analyzed for |
| 5 | 120 μl | 300 μl | Sacch. + Ferment | as (2) |
| 6 | 120 μl | 300 μl | Sacch. + Ferment | as (3) + gluco-amylase activity |

The results of the analyses for the different runs are shown in the drawings as FIGS. 2–6. The amylase content in the liquid for runs 2 and 3 were about the same as is illustrated for runs 5,6.

The alcohol content in the fermentations has been analyzed (%w/w) and is tabulated below.

| | FERMENTATION TIME | | | | |
|---|---|---|---|---|---|
| Run | 24 h | 48 h | 72 h | 216 h | 216 h |
| 3 | 1.19% | 1.65% | 2.59% | 3.60% | 3.66% (run 2) |
| 6 | 2.96 | 5.43% | 7.40% | 8.28% | 8.32% (run 5) |

EXAMPLE 10

This example illustrates the possibility of submitting unreacted granular starch from a fermentation to a new fermentation after separation of starch and yeast from the aqueous phase.

A 40% starch slurry (150 g final weight), ph 4.5, with 40 μl Fungamyl ® 800 L, 100 μl AMG 150 L, yeast and yeast extract as in Example 9, is fermented at 30° C.

After 48 h, the unreacted starch and yeast is allowed to sediment. The aqueous phase is decanted off. To each fermentation flask an amount of starch is added of about 2× the $CO_2$ losses (this brings the starch slurry concentration back to about its original value).

10 μl Fungamyl ® are added (to make up for the 25% alpha-amylase disappearing with the aqueous phase) and 100 μl AMG 150 L are added (as the glucoamylase is mainly lost with the aqueous phase).

The flasks are made up to 150 g with water. The fermentation is continued without addition of new yeast (the yeast sediments with the granular starch). The fermentation is followed by $CO_2$ weighing analyses.

| | First Fermentation | | | Second Fermentation | |
|---|---|---|---|---|---|
| | $CO_2$ losses | | Alc. % w/w | Starch | $CO_2$ losses |
| Run | 24 h | 48 h | 48 h | Added | 21 h | 45 h |
| 1 | 3.62 g | 8.29 | 8.60% | 16.6 g | 2.19 g | 5.59 |
| 2 | 4.78 g | 10.02 | 10.21% | 20.0 g | 4.60 g | 5.38 |
| 3 | 5.49 g | 10.61 | 10.37% | 21.2 g | 4.62 g | 4.83 |
| 4 | 4.88 g | 10.09 | 9.94% | 20.2 g | 4.65 g | 5.46 |
| 5 | 3.83 g | 8.93 | 8.85% | 17.9 g | 4.32 g | 4.80 |

The above results can be explained as follows:

Initially, 60 g of starch were present (90 percent dry matter) corresponding to 54 g of starch d.s.b. The starch consumed in the first fermentation is 22.75 g (glucose)×0.9=20.5 g. This leaves about 33.5 g dry starch in the 140 g left in the fermentation broth after generation and release of about 10 g of $CO_2$. The water-alcohol in liquid phase in the mixture will be about 110 ml, thus leaving about 40 g of water phase with an alcohol content of about 10 percent after the decantation removal of about 70 g of aqueous phase. About 50 g of water was added for the water makeup to the (second) fermentation.

Since 10 percent alcohol is near the toxic limits to the fermentation, a $CO_2$ loss in the second fermentation of about half of the $CO_2$ loss in the first fermentation is all that could be expected, and in fact, no more was obtained during fermentation for 45 hours. Over the first 24 hours of fermentation both fermentations generated $CO_2$ at about the same rate, indicating thereby comparable enzyme activity levels in the fermenting slurries.

EXAMPLE 11

The purpose of this experiment is to show the influence of dry matter content of the granular starch slurry on the fermentation rate.

Each flask contains 150 g total weight. Yeast and yeast extract as in Example 9.

| | | Enzyme Dosage | | Weight Losses as $CO_2$ | | | | | % |
|---|---|---|---|---|---|---|---|---|---|
| Run No. | Starch Content | Fungamyl® 800 L | AMG 150 L | 24 h | 48 h | 71 h | 95 h | 167 h | Starch Conv. 167 h |
| 1 | 10% | 10 μl | 25 μl | 0.92 | 1.94 | — | 3.94 | — | 70% |
| 2 | 20% | 20 μl | 50 μl | 2.23 | 3.66 | 5.04 | 6.24 | 9.48 | 78.5% |
| 3 | 25% | 25 μl | 62.5 μl | 2.95 | 5.34 | 7.38 | 9.08 | 12.63 | 81.1% |
| 4 | 30% | 30 μl | 75 μl | 3.30 | 5.74 | 7.93 | 9.82 | 12.40 | 66.7% |
| 5 | 40% | 40 μl | 100 μl | 3.72 | 6.52 | 8.67 | 9.48 | 9.50 | 57.2% |

To avoid possible confusion about the details of practice of this invention, the carbohydrate nutrient has always been posed hereinabove as granular starch. Such reference only to granular starch is not intended as reference solely to starch in the separated out relatively pure forms (e.g., cornstarch, potato starch) widely available in commerce. The other forms of starch heretofore employed in fermentation practice, including, for example, corn grits, degerminated grains, cracked grains, even whole grains are directly fermentable according to the above described practice of this invention, and the term granular starch as employed in the claims hereinafter is intended to include within its scope, all starch in all forms.

I claim:

1. A fermentation process which conists essentially of fermenting a 10%–45% w/w aqueous slurry of granular starch for the production of ethanol with an ethanol producing microorganism in the presence of alpha-amylase and gluco-amylase, the conduct of said fermentation being characterized by low levels of dextrin and fermentable sugars in solution in the fermentation broth throughout the fermentation, and, thereafter recovering enzymes from the fermentation broth for use anew in fermentation of granular starch.

2. The fermentation process of claim 1 wherein the process further comprises halting the fermentation prior to complete disappearance of granular starch, and thereafter recovering residual granular starch from the fermentation broth for later fermentation, enzymes being recovered on the residual starch.

3. The fermentation process of claim 1 carried out with a near to linear generation of $CO_2$ during the main course of the fermentation.

4. The fermentation process of claim 1 wherein the starch content of the slurry is in the range of 25–45% w/w and the granular starch and alcohol producing microorganism are removed from the fermentation broth for later fermentation, the enzymes being recycled with the granular starch.

5. The fermentation process of claim 1 wherein a thermostable alpha-amylase is employed and de-alcoholized fermentation broth is used anew in fermentation of granular starch, the de-alcoholized fermentation broth containing therein active alpha-amylase.

6. The fermentation process of claim 1 wherein the granular starch is pretreated with at least one of said enzymes at temperatures not exceeding the initial gelatinization temperature of starch prior to the fermentation.

7. A fermentation process which consists essentially of fermenting a 10%–45% w/w aqueous slurry of granular starch for the production of ethanol with an ethanol producing microorganism in the presence of alpha-amylase and gluco-amylase, the conduct of said fermentation being characterized by low levels of dextrin and fermentable sugars in solution in the fermentation broth throughout the fermentation, and a near to linear rate of $CO_2$ generation during the main course of the fermentation.

8. A fermentation process which consists essentially of fermenting a 10%–45% w/w aqueous slurry of granular starch for the production of ethanol at a temperature in the range of 25°–38° C. with an ethanol producing microorganism in the presence of fungal alpha-amylase in amounts within the range of 0.02–2.0 FAU/g of starch in the slurry or Bacillus amylase in the amount of 0.01–0.6 KNU/g of starch in the slurry and gluco-amylase in amounts within the range of 0.05–10.0 AGU/g of starch in the slurry, the conduct of said fermentation being characterized by low levels of dextrin and fermentable sugars in solution in the fermentation broth throughout the fermentation, and generation of $CO_2$ at a near to linear rate during the main course of the fermentation, and, thereafter recovering enzymes from the fermentation broth for use anew in fermentation of granular starch.

* * * * *